United States Patent [19]

Staniforth

[11] 4,349,542
[45] Sep. 14, 1982

[54] MIXTURE CONTAINING ACTIVE INGREDIENT AND DENDRITIC CRYSTALLINE SUGAR FOR TABLETING

[75] Inventor: John N. Staniforth, Birmingham, England

[73] Assignee: National Research Development Corporation, London, England

[21] Appl. No.: 156,783

[22] Filed: May 5, 1980

[30] Foreign Application Priority Data

Jun. 8, 1979 [GB] United Kingdom ............... 7920125

[51] Int. Cl.³ .................. C13K 5/00; C13K 11/00; C13K 13/00
[52] U.S. Cl. .................. 424/153; 127/29; 127/31; 127/60; 127/63; 264/109; 264/122; 424/230; 424/361
[58] Field of Search ............... 127/31, 60; 127/63, 29; 424/14; 264/109, 122

[56] References Cited

U.S. PATENT DOCUMENTS

| | | | |
|---|---|---|---|
| 3,169,888 | 2/1965 | Ryan | 127/29 X |
| 3,337,404 | 8/1967 | Polli | 424/153 X |
| 3,344,030 | 9/1967 | Stevens | 424/14 X |
| 3,445,283 | 5/1969 | Amano | 127/63 X |
| 3,446,899 | 5/1969 | Cavalli | 424/12 X |
| 3,533,805 | 10/1970 | Nava | 127/31 X |
| 3,619,292 | 11/1971 | Brouillard | 127/29 |
| 3,627,583 | 12/1971 | Troy | 127/29 |
| 3,639,169 | 2/1972 | Broeg | 127/29 |
| 3,639,170 | 2/1972 | Hutton | 127/31 |
| 3,642,535 | 2/1972 | Graham | 127/29 |
| 3,721,585 | 3/1973 | Francis | 127/60 |
| 3,746,554 | 7/1973 | Endicott | 127/31 X |
| 3,873,694 | 3/1975 | Kanig | 127/63 X |
| 3,903,255 | 9/1975 | Gusman | 424/153 X |
| 3,961,004 | 6/1976 | Nasir | 424/361 X |
| 4,013,775 | 3/1977 | Nelson | 424/361 X |
| 4,265,847 | 5/1981 | Hunt | 264/122 |

*Primary Examiner*—Sidney Marantz
*Attorney, Agent, or Firm*—Oblon, Fisher, Spivak, McClelland & Maier

[57] ABSTRACT

An excipient for tableting of powder mixtures, e.g. pharmaceutical powder mixtures comprises particles of an inert solid material, said particles being of average particle size in the range from 50-1,000 μm in diameter and having surface pores of at least 10 μm in diameter. Preferred excipients comprising dendritic spherulites of sugars e.g. fructose, mannitol or lactose, are prepared by crystallization of sugars under conditions of high crystallization pressure; for instance on addition of crystallizing agents, e.g. ethanol, and/or seeding materials to saturated sugar solutions. The excipients are mixed with finely divided active ingredients e.g. micronized drug particles, and tableted to produce tableted products. The new excipients are suitable for use in direct compression tableting techniques and advantageously diminish problems of excipient/active ingredient segregation during handling of the excipient/active ingredient mixtures.

22 Claims, No Drawings

MIXTURE CONTAINING ACTIVE INGREDIENT AND DENDRITIC CRYSTALLINE SUGAR FOR TABLETING

This invention relates to tableting of powder mixtures, and in particular to tableting of pharmaceutical powder mixtures.

Pharmaceutical tablets comprise an active ingredient typically mixed with an inert excipient, such as powdered cellulose or sugars, to give the tablets bulk. Such tablets are made by either powder granulation techniques, in which an active ingredient/excipient powder mix is formed into granules before compression, or by direct compression of the powder mix. Powder granulation techniques, which include both wet and dry granulation techniques, are very widely used but are not altogether satisfactory in view of high plant costs and extended processing times. Additionally wet granulation techniques cannot be used successfully with heat- and moisture-sensitive active ingredients as these may deteriorate during processing.

Plant costs and processing times are generally lower when using direct compression tableting techniques, but segregation of the active ingredient/excipient powder mixture can take place during processing leading to a lack of uniformity in the tableted product which is undesirable and may even be dangerous, for instance, when the active ingredient is a highly potent drug. Segregation problems arise because of a difference in the size requirements of the two components of the powder mix; it is generally desirable that the excipient particles be above a minimum size so that the materials are sufficiently free-flowing for normal processing, whereas the active ingredient particles must normally be of smaller size to promote satisfactory mixing. In view of these segregation problems direct compression tableting techniques have not generally been as widely adopted as granulation tableting techniques.

A new pharmaceutical tableting excipient has now been discovered which is suitable for use in direct compression tableting techniques and advantageously diminishes problems of segregation of excipient and active ingredient during handling of the material.

According to the present invention a new excipient for tableting of powder mixtures comprises particles of an inert solid material, said particles being of average particle size in the range from 50–1,000 μm in diameter and having surface pores of at least 10 μm in diameter.

The invention also includes processes for the production of tablets in which active ingredient is mixed with the excipient of the invention and fabricated into tablets, and furthermore includes tableted products comprising active ingredient mixed with the excipient of the invention.

The excipient may be used for tableting in general, where a high level of uniformity in the concentration of active ingredient in the tableted product is required in particular for direct compression tableting; the surface pores of the excipient particles advantageously providing sites for holding particles of active ingredient and thereby diminishing the tendency for active ingredient-excipient segregation. It will be appreciated, therefore, that the size of the surface pores may be varied in accordance with the size of active ingredient particles, though generally the surface pores are of maximum size less than 100 μm in diameter, preferably less than about 60 μm in diameter. In particular the excipient of the invention is suitable for use in pharmaceutical tableting, especially by direct compression tableting techniques. The excipient may be used for tableting pharmaceutical active ingredients in general, including antibiotics, and thus excipients for these uses are typically pharmaceutically acceptable materials. The pharmaceutical active ingredient particles which are mixed with the excipient are generally in highly finely divided form, for instance in the form produced by micronisation procedures, and usually have a maximum particle size of about 40–50 μm in diameter.

The excipient particles are normally of rough and preferably highly re-entrant surface structure, and in one form may comprise spherulites e.g. dendritic spherulites, of suitable inert materials, usually pharmaceutically acceptable inert materials. Preferably the excipient comprises a sugar; for instance, in the form of spherulites especially dendritic spherulites of sugars such as fructose, mannitol or especially lactose.

Preferred dendritic sugar spherulites may be prepared by crystallisation of sugars under conditions of high crystallisation pressure. For instance, dendritic sugar spherulites may be prepared by crash crystallisation from saturated aqueous solutions of sugars, especially on addition of a crystallising agent to the saturated solution. Such crystallising agents typically comprise liquids which are miscible with water but in which the sugar is relatively insoluble. For example, a highly satisfactory crystallising agent for use in the preparation of dendritic spherulites of lactose is ethanol, e.g. in the form of IMS, in which lactose is relatively insoluble, i.e. lactose has a solubility in ethanol of about 0.5%. Other suitable crystallising agents include other alcohols such as propan-1-ol or propan-2-ol or methanol, and ketones such as acetone. Crystallisation of sugars from saturated solutions may be initiated by addition of seeding material e.g. crystals of the sugar in solution, and such seeding may preferably be used in combination with addition of a crystallisation agent as above. Seeding of the saturated solution advantageously gives rise to increased bulk density for the crystallised excipient particle product desirably giving rise to good flow and handling properties for the material.

The size and morphology of the spherulites produced on crystallisation of sugars from saturated solutions may be varied by controlling the conditions pertaining during crysallisation and the period of crystal growth. Usually, the crystals are grown at room temperature e.g. about 20° C. over a period of up to a few hours, usually from about ½ up to about 2½ hours, preferably about 1½ hours. Especially, however, the form of the spherulites may be varied by varying the proportion of crystallising agent e.g. ethanol, which is added to the saturated solution of the sugar. Thus, for example, particularly preferred forms of lactose spherulites are prepared from saturated lactose solution by addition of ethanol as a crystallising agent, e.g. in the form of IMS, to give a mother liquor comprising from 60–90% preferably from 70–80% by volume of ethanol. Also, for example, preferred forms of mannitol spherulites are produced by crystallisation from saturated mannitol solutions by addition of ethanol as a crystallising agent to give mother liquors comprising from 10 to 90%, preferably about 10%, by volume of ethanol.

The preferred dendritic spherulites which are formed on crash crystallisation of sugars from saturated solutions are formed by agglomeration of single dendritic crystals of the sugars e.g. lactose, to form dendritic spherulites. It will be appreciated, therefore, that it is necessary to avoid undue agitation of the crystals during crystal growth and the agitation used is typically not so severe as to cause substantial break up the spherulites and give rise to the production of single dendritic crystals only. It is desirable, however, to subject the growing crystals to sufficient agitation to prevent the formation of a solid cake of crystals. This agitation may be either mechanical or ultrasonic agitation. The agitation used is preferably intermittent agitation e.g. agitation for one minute every 15 minutes during crystal growth, or slow, gentle continuous agitation.

After crystal growth the spherulites may be recovered by filtration and are usually washed e.g. with acetone, to remove excess mother liquor prior to drying. After drying, the sperulites may then be sized, for instance by sieving through a screen of suitable mesh size e.g. mesh diameter of about 700μ to provide a particulate excipient which is ready for use for blending with active ingredients as required.

Generally low shear rate mixers, such as tumble mixers, are used for blending of active ingredient e.g. micronised drug particles, with the dendritic spherulite excipient particles of the invention, in view of the tendency of these spherulites to break down to single dendrites under stress. The excipient and active ingredient mix may then be tableted as desired. Preferably the excipient particles are sufficiently free flowing for handling by direct compression tableting techniques without need for addition of glidants or for granulation prior to tableting.

In order to increase the holding power of the excipient for the active ingredient particles it may be desirable to charge the excipient particles and/or active ingredient particles before mixing with the active ingredient. Such charging of the excipient particles may be conveniently effected tribo-electrically, or if necessary by means of a corona discharge. For charging, it may be desirable to coat the excipient particles with a substance, usually a polymeric material, which facilitates the establishment of a net charge, especially a positive charge, on the particles e.g. with a substance such as polyvinylpyrollidone. Charged excipient particles advantageously hold on to the active ingredient particles more strongly than uncharged particles. The excipient and active ingredient particles, whether charged or not, may be conveniently mixed with the active ingredient particles in a suitable contactor, for instance, in a fluidised bed contactor in which the active ingredient particles e.g. micronised drug particles may be fed from a cyclone on to the excipient particles.

In addition to facilitating the establishment of a net charge on the excipient particles, additives, generally polymeric additives, may be added to the excipient to strengthen the excipient particles. Such strengthening of the excipient particles advantageously diminishes breakdown of the particles during processing giving rise to increased retention of desirable flow and adhesive properties. Polymeric additives and other additives may be incorporated into the bulk of the excipient material, for instance, by dissolving or dispersing the additive in the mother liquor prior to crystallisation of the excipient. Preferably, however, the polymeric or other additive is coated onto the excipient particles after preparation, e.g. after crystallisation from the mother liquor. Suitable polymeric additives for both charging and strengthening purposes include polyvinylpyrrolidone and similar polymeric materials.

Compression of the excipient-active ingredient mixture may be carried out by any suitable means to give tablets as required.

The invention is further described by way of illustration only in the following Examples which relate to the production of dendritic spherulites of lactose and mannitol and investigation of the properties of these spherulites.

EXAMPLE 1

Lactose Excipient

An excipient suitable for use in direct compression tableting was prepared from lactose.

Lactose powder (lactose Ph.Enr. supplied by Whey Products Ltd., Royal London House, London, U.K.) as dissolved in water at 70° C. to produce a supersaturated mother liquor, which was then allowed to equilibrate for 10 minutes to remove crystal ghosts. Dendritic spherulites of lactose were then obtained from the mother liquor by crash crystallisation on addition of solutions of ethanol (industrial methylated spirits, supplied by Fisons Scientific Apparatus Ltd., Loughborough, U.K.) to aliquots of the mother liquor, followed by crystal growth at 25° C. The growing crystals were agitated during crystal growth to prevent the formation of a solid cake of crystals, though care was taken not to break up the spherulites into single dendritic crystals. The growing crystals were either stirred mechanically or vibrated ultrasonically either intermittently (1 minute every 15 minutes) or very gently continuously.

Several batches of crystalline dendritic spherulite agglomerates were produced, the crystals being grown in flasks surrounded by water at 25° C. in a constant temperature bath. Mother liquors containing 40, 50, 60, 70, 80 and 90% w/w ethanol were used to prepare crystals which were recovered after 5, 15, 30, 60 and 90 minutes of crystal growth. The crystal agglomerates were recovered by filtration using a Buchner flask and funnel on filter paper (Whatman, Number 1, Whatman Ltd., London, U.K.). Secondary growth, which occurs from the residual mother liquor surrounding the filtered crystals and causes caking during drying, was avoided by washing with pure acetone. The washed crystals were dried in a vacuum oven (Edwards High Vacuum, London, U.K.) at a pressure of 250 mm of mercury and 70° C.

The dried crystals were carefully passed through a 500 μm wire mesh test sieve and the yields from each batch were calculated.

Further batches of crystals were also prepared using a variation of the method described above. In these batches the mother liquor was seeded with 0.5% w/w lactose crystals of diameter less than 60 μm, and crystals were recovered after 90 minutes. Filtration was carried out in two stages: A 53 μm sieve (Endecotts Ltd) was used to collect the larger agglomerates which blocked the back-up filter, the smaller crystals being removed in a Buchner filter funnel. Following drying the crystal agglomerates were screened on an 850 μm test sieve. Any agglomerates still retained after ten minutes's shaking were transferred to a wire mesh processing sieve and gently brushed through. Using a sieve shaker, operated for twenty minutes, crystals in these batches were separated into six size fractions ranging from 1000 μm to less than 45 μm (Endecotts Ltd. London, England).

The properties of the crystal agglomerates produced above were investigated; for instance specific surface areas were determined by low temperature gas adsorption; and pore volume distributions, size distributions, shapes and absolute densities and accessible surface areas were investigated by mercury intrusion porosimetry. It was found that spherulites were formed with varying surface properties, but with similar flow properties. The surface properties of particles were characterised by shape, pore structure and surface area measurements. Consideration of the crystallisation yields and surface area measurements shown that crystal recovery after 90 minutes produced the optimum difference in crystal properties. Shape factor analysis indicated that the most irregular spherulites were produced from mother liquors containing 70-80% ethanol. Mercury porosimetry showed that spherulites with the largest pore volumes were produced from 80% ethanol solutions (i.e. with an average pore size in the range from 10 $\mu$m to 100 $\mu$m) and that the number distribution of large pores in each particle size fraction reached a maximum for spherulites collected from solutions containing between 70 and 80% ethanol. Surface areas of the spherulites, measured by nitrogen adsorption, reached a maximum in samples crystallised from 80% ethanol. The surface area of pores, accessible to particles with diameters larger than 2 $\mu$m, were also greatest for spherulites recovered from 80% ethanol solutions. Finally Stereophotomicrographs showed a distinct change in surface morphology between those lactose spherulites recrystallised from ethanol concentrations below 70% and those above 80%.

From the results obtained it was expected that spherulites of lactose recrystallised from 70% ethanol solution would possess a surface structure which is particularly well adapted for trapping small drug particles when the lactose is used as an excipient in tabletting. The spherulites were therefore subjected to vibration testing in a model drug system using finely divided potassium chloride particles (average particle size in the range 10-100 $\mu$m) and results were compared with those of similar tests using Dipac, a commercially available direct compression tabletting sugar. It was found that the commercially available material was considerably less stable to segregation under vibration conditions, whereas the lactose was virtually free from stability problems.

EXAMPLE 2

Similarly an excipient, suitable for direct compression tabletting, was prepared by recrystallisation of mannitol.

A supersaturated solution of mannitol was prepared and mannitol crystals (from 5-10% of the final bulk) were added to seed the solution. Mannitol was crash-crystallised from solution by addition of ethanol (I.M.S.), the preferred ethanol addition being about 10% w/w of the resultant mother liquor and crystal agglomerates were grown over a period of about 1½ hours at 25° C. the mother liquor being stirred intermittently (for about 1 minute every 30 minutes) to prevent caking. The resultant crystal agglomerates were recovered by filtration, washed with acetone or alcohol to remove remaining mother liquor and dried in a hot air oven on trays. Although most of the mother liquor was removed from the crystals by washing some remained giving rise to caking after drying. The dendritic spherulite crystal agglomerates were therefore reduced to a manageable size by screening through a 1 mm mesh sieve.

Dendritic spherulites of lactose and mannitol, as prepared above, are used as excipients for pharmaceutical tabletting in the usual manner. For instance micronised drug particles (e.g. having average particle sizes in the range 10-100 $\mu$m) are mixed with the dendritic spherulites in a low shear rate mixer such as a tumble mixer, and the mix is then fabricated into tablets, especially by direct compression tabletting techniques.

EXAMPLE 3

Crystallite lactose as prepared in example 1 by crystallisation from a mother liquor containing 70% by volume of ethanol, was compared with two commercially available direct compression tabletting excipients. Various physical parameters of the excipient were first determined and then the excipients were compared in segregation experiments.

Characterisation of physical parameters excipients used in segretation experiments The three excipients were tested: 1. Crystallite lactose, 2. Dipac (a direct-compacting sugar, supplied by Wilfred Smith Fine Chemicals Ltd., Edgware, U.K.; manufactured by Amstar Corp, Avenue of the Americas, New York, U.S.A.) and 3. Emdex (a spray-crystallised, maltose-dextrose direct tabletting sugar, supplied by K & K-Greeff Fine Chemicals Ltd., Croydon, U.K.; manufactured by Edward Mendell, New York, U.S.A.)

The two commercially available excipients were tested in the form in which they were received from the manufacturers. Particular attention was given to the surface characteristics of the excipient powders especially those properties, such as porosity, which would influence the entrapment of fine drug powder particles. The results obtained are given in Table 1 below:

TABLE 1.1

| | Particle densities | | |
|---|---|---|---|
| Excipient | Poured bulk density (g . ml$^{-1}$) | Consolidated bulk density (g . ml$^{-1}$) | True density (g . ml$^{-1}$) |
| Dipac | 0.69 | 0.75 | 1.24 |
| Emdex | 0.68 | 0.72 | 1.24 |
| Crystallite lactose (250-500$\mu$m particle size) | 0.39 | 0.48 | 0.46 |

TABLE 1.2

| Intraparticle pore volumes (determined by mercury penetration porosimetry) | |
|---|---|
| Excipient | Pore volume (ml . g$^{-1}$) |
| Dipac | 0.10 |
| Emdex | 0.64 |
| Crystallite lactose (250-500$\mu$m particle size) | 1.25 |

TABLE 1.3

| Surface area (determined by multipoint B.E.T. analysis) | |
|---|---|
| Excipient | Surface area (cm$^2$ . g$^{-1}$) |
| Dipac | 1,780 |
| Emdex | 1,170 |
| Crystallite lactose (250-500$\mu$m particle size) | 5,600 |

TABLE 1.4

| Surface roughness (rugosity) | |
|---|---|
| Excipient | Rugosity (dimensionless) |
| Dipac | 5.56 |
| Emdex | 3.35 |
| Crystallite lactose (250–500μm particle size) | 14.61 |

TABLE 1.5

Surface area accessible to fine adherent particles (Accessible Surface Areas)

| | Accessible surface area ($cm^2 \cdot g^{-1}$) | |
|---|---|---|
| Excipient | >2μm | >10μm |
| Dipac | 817 | — |
| Emdex | 1,985 | — |
| Crystallite lactose | 4,848 | 583 |

TABLE 1.6

| Moisture content (% wet basis) | |
|---|---|
| Excipient | Loss on drying (%) |
| Dipac | 0.1 |
| Emdex | 6.1 |
| Crystallite lactose | 0.1 |

Vibrational segregation tests

The three excipient powders were mixed with 0.5% by weight model drug (fine potassium chloride powder <45 μm) to form ordered mixes in which the K Cl particles were held on the surface of the coarse excipient particles. The model drug/excipient mixtures were then subjected to various vibration treatments and the extent of segregation determined by measuring the K Cl concentration present in samples of the mixes. The vibration intensity was varied by altering the vibration frequency and acceleration and the different drug and excipient mixes were examined to find their ability to resist segregation. The coefficient of variation of 20 powder samples weighing 200 mg ±0.5 mg was determined to assess the homogeneity of the drug and excipient mixes. Coefficients of variation (CV) below 2% following vibration were considered to meet pharmacopeial requirements and therefore were not segregated. Any drug with CV greater than 2% was considered to have become segregated from its excipient powder. Marked segregation was considered to have occurred in drug and excipient mixes with a CV larger than 5% following vibration. The most intense segregation conditions were produced by low frequencies (less than 50 Hz) and high accelerations (larger than 2 G). Drug and excipient powders which remained mixed under these vibration conditions were considered to be extremely stable and unlikely to segregate during normal processing in manufacture of tablets or capsules or other powder manipulations. Different combinations of vibration frequency and acceleration were used to test the ability of the different drug and excipient mixes to withstand segregation when vibrated for different lengths of time. The longer the powders were vibrated the more intense the pressure for drug particles to segregate from excipient particles. Only the most intense conditions are reported here in powders vibrated for one hour at 20 Hz and 50 Hz frequency and an acceleration of 3 G. The results obtained and particulars of tests carried out are given in Table 2 below.

TABLE 2.1

| | Coefficients of variation of drug and excipient mixes following vibration for one hour at 3G and two frequencies: | |
|---|---|---|
| Excipient | 20 Hz | 50 Hz |
| Dipac | 65.52% | 32.11% |
| Emdex | 0.70% | 1.83% |
| Crystallite lactose | 0.71% | 2.57% |

TABLE 2.2

The ability of the different excipient powders to form non-segregating mixes with higher percentages of drug powder was tested following vibration at 2G and 50Hz.

| | Coefficient of variation in mixes of different concentrations of drug powder | | | |
|---|---|---|---|---|
| Excipients | ½% | 1% | 2% | 5% |
| Dipac | 21.50 | 81.8 | 139.02 | 256.67 |
| Emdex | 1.23 | 24.3 | 124.66 | 187.87 |
| Crystallite lactose | 1.64 | 11.28 | 31.12 | 55.56 |

TABLE 2.3

Different particle sizes of crystallite lactose powders were tested for their ability to withstand segregation from drug powders with which they were mixed. Even at the largest crystallite lactose powder particle size, the excipient was able to prevent segregation of drug powder following vibration at high frequency.

| Crystallite lactose Particle size (μm) | Vibration frequency (Hz) | Coefficient of variation (%) |
|---|---|---|
| 9.5 μm | 30 | 0.02 |
| | 50 | 0.06 |
| | 100 | 0.04 |
| | 200 | 0.01 |
| | 500 | 0.01 |
| | 1000 | 0.04 |
| | 5000 | 0.03 |
| 127 μm | 30 | 0.32 |
| | 50 | 0.13 |
| | 100 | 0.04 |
| | 200 | 0.07 |
| | 500 | 0.03 |
| | 1000 | 0.03 |
| | 5000 | 0.06 |
| 212 μm | 30 | 1.36 |
| | 50 | 0.12 |
| | 100 | 0.88 |
| | 200 | 0.16 |
| | 500 | 0.03 |
| | 1000 | 0.02 |
| | 5000 | 0.03 |
| 354 μm | 30 | 3.09 |
| | 50 | 3.65 |
| | 100 | 1.08 |
| | 200 | 1.04 |
| | 500 | 0.17 |
| | 1000 | 0.02 |
| | 5000 | 0.04 |
| 596 μm | 30 | 14.63 |
| | 50 | 16.07 |
| | 100 | 9.01 |
| | 200 | 5.99 |
| | 500 | 0.99 |
| | 1000 | 0.71 |
| | 5000 | 0.36 |
| 843 μm | 30 | 21.15 |
| | 50 | 19.57 |
| | 100 | 11.24 |
| | 200 | 8.09 |
| | 500 | 3.67 |
| | 1000 | 0.89 |
| | 5000 | 0.43 |

TABLE 2.4

As an alternative the comparison of the extent of segregation of a mix following vibration with the homogeneity of a completely mixed powder can be expressed by way of a coefficient which varies from 0 to 1. A value of unity indicates a completely homogeneous powder where no segregation has occurred. The results obtained for model drug and excipient powder vibrated at 50 Hz frequency and 0.75G acceleration are given below.

| Excipient | Scale of segregation (1 = totally mixed) |
|---|---|
| Dipac | 0.65 |
| Emdex | 0.73 |
| Crystallite lactose | 0.95 |

In addition to measuring the segregation tendency of drug and excipient powder mixes during vibration, the adhesive force which bind fine drug particles to coarse excipient particles were quantified. The higher the proportion of fine drug particles adhering to coarse particles at particular forces, the greater the stability of the ordered mix between the two constituent sets of powder particles. These adhesion forces were measured in a cell fitted into an ultracentrifuge rotor; the speed of rotation of the cell being equated with certain adhesion forces. It became clear that excipient powders which were able to hold large quantities of drug particles at high adhesion forces formed ordered mixes which were capable of resisting segregation. Forces less than 38 m.dynes binding small drug particles to coarser excipient particles were equivalent to the ordered mixes being subjected to separation (segregation) forces of approximately 143,000 dyne. $g^{-1}$. Excipient particles which lost large quantities of weakly bound drug particles at these low separation forces were found to form unstable, segregating ordered mixes.

The results obtained for ordered mixes with various excipients containing 1%, 2% and 5% by weight of salicyclic acid as model drug are given below in Table 3. The results show that as the amount of model drug present in the mix varies, the holding capacity of the excipients changes.

TABLE 3

| Excipient | Percentage of "drug" particles removed from excipient by separation forces less than 143,000 dynes $g^{-1}$ for 3 drug concentrations | | |
|---|---|---|---|
| | 1% "drug" | 2% "drug" | 5% "drug" |
| Sucrose | 8% | 18% | 21.8% |
| Dipac | 20.3% | 25% | 28% |
| Emdex | 2% | 8.8% | 22% |
| Crystallite lactose (250–500μm) | 7.6% | 5.3% | 13.5% |
| Crystallite lactose (500–710μm) | 3.8% | | |

I claim:

1. A process for preparing a tablet comprising an active ingredient and an excipient, said process comprising mixing an active ingredient and an excipient comprising particles of a dendritic crystalline sugar, said particles being of average particle size in a range from 50–1000 μm in diameter and having surface pores of at least 10 μm in diameter, and subjecting said mixture to direct compression tableting.

2. A process according to claim 1 wherein the surface pores are of maximum size less than 100 μm in diameter.

3. A process according to claim 1 wherein the active ingredient has a maximum particle size of about 50 μm in diameter.

4. A process according to claim 1 wherein the particles comprise dendritic spherulites.

5. A process according to claim 1 wherein the sugar is selected from the group consisting of fructose, mannitol and lactose.

6. A process according to claim 1 wherein the excipient additionally comprises a polymeric additive.

7. A process according to claim 1 wherein the active ingredient comprises a pharmaceutically active substance and the excipient comprises a pharmaceutically acceptable material.

8. A process according to claim 1 wherein the excipient particles and/or active ingredient particles are electrically charged prior to mixing.

9. A process according to claim 8 wherein the excipient particles are coated with a substance which facilitates the establishment of an electric charge on the particles.

10. A pulverulent mixture utilizable in the direct compression tableting of tablets comprising an active ingredient and an excipient, said mixture comprising as the excipient particles of a dendritic crystalline sugar, said particles being of average particle size in a range of from 50–1000 μm in diameter and having surface pores of at least 10 μm in diameter.

11. A mixture according to claim 10 wherein the surface pores are of maximum size less than 100 μm in diameter.

12. A mixture according to claim 10 wherein the active ingredient has a maximum particle size of about 50 μm in diameter.

13. A mixture according to claim 10 wherein the particles comprise dendritic spherulites.

14. A mixture according to claim 10 wherein the sugar is selected from the group consisting of fructose, mannitol and lactose.

15. A mixture according to claim 10 wherein the excipient additionally comprises a polymeric additive.

16. A mixture according to claim 10 wherein the active ingredient comprises a pharmaceutically active substance and the excipient comprises a pharmaceutically acceptable material.

17. A tableted product produced by the process of claim 1.

18. A tableted product according to claim 17 wherein the sugar is selected from the group consisting of fructose, mannitol and lactose.

19. A tableted product according to claim 17 wherein the active ingredient comprises a pharmaceutically active substance and the excipient comprises a pharmaceutically acceptable material.

20. A tableted product produced by direct compression tableting of the pulverulent mixture of claim 10.

21. A tableted product according to claim 20 wherein the sugar is selected from the group consisting of fructose, mannitol and lactose.

22. A tableted produce according to claim 20 wherein the active ingredient comprises a pharmaceutically active substance and the excipient comprises a pharmaceutically acceptable material.

* * * * *

UNITED STATES PATENT AND TRADEMARK OFFICE
CERTIFICATE OF CORRECTION

PATENT NO. : 4,349,542

DATED : September 14, 1982

INVENTOR(S) : John N. Staniforth

It is certified that error appears in the above-identified patent and that said Letters Patent is hereby corrected as shown below:

On the title page,
Please correct as follows:

[22] -- Filed: June 5, 1980 --

Signed and Sealed this

Eighth Day of March 1983

[SEAL]

Attest:

GERALD J. MOSSINGHOFF

Attesting Officer

Commissioner of Patents and Trademarks